United States Patent
Calhoun

(10) Patent No.: US 7,704,520 B1
(45) Date of Patent: Apr. 27, 2010

(54) METHODS OF PROMOTING ENHANCED HEALING OF TISSUES AFTER CARDIAC SURGERY

(75) Inventor: Christopher J. Calhoun, San Diego, CA (US)

(73) Assignee: MAST Biosurgery AG, Zurich (CH)

( * ) Notice: Subject to any disclaimer, the term of this patent is extended or adjusted under 35 U.S.C. 154(b) by 227 days.

(21) Appl. No.: 10/660,461

(22) Filed: Sep. 10, 2003

Related U.S. Application Data

(60) Provisional application No. 60/429,166, filed on Nov. 25, 2002, provisional application No. 60/409,459, filed on Sep. 10, 2002.

(51) Int. Cl.
*A61F 2/00* (2006.01)

(52) U.S. Cl. .................................................. 424/423

(58) Field of Classification Search ........................ None
See application file for complete search history.

(56) References Cited

U.S. PATENT DOCUMENTS

| | | | |
|---|---|---|---|
| 3,636,956 A | 1/1972 | Schneider | |
| 3,874,986 A | 4/1975 | Browall et al. | |
| 4,464,320 A | 8/1984 | Saidla | |
| 4,603,695 A | 8/1986 | Ikada et al. | |
| 4,769,038 A | 9/1988 | Bendavid et al. | |
| 4,955,907 A | 9/1990 | Ledergerber | |
| 5,030,220 A | 7/1991 | Howland | |
| 5,047,054 A | 9/1991 | Vijayan et al. | |
| 5,227,412 A | 7/1993 | Hyon et al. | |
| 5,270,300 A | 12/1993 | Hunziker | |
| 5,380,329 A | 1/1995 | Elia et al. | |
| 5,412,068 A | 5/1995 | Tang et al. | |
| 5,437,672 A | 8/1995 | Alleyne | |
| 5,525,646 A | 6/1996 | Lundgren et al. | |
| 5,609,629 A | 3/1997 | Fearnot et al. | |
| 5,626,861 A | 5/1997 | Laurencin et al. | |
| 5,679,723 A | 10/1997 | Cooper et al. | |
| 5,686,090 A | 11/1997 | Schilder et al. | |
| 5,759,190 A | 6/1998 | Vibe-Hansen et al. | |
| 5,776,195 A | 7/1998 | Derycke | |
| 5,795,584 A * | 8/1998 | Totakura et al. | 424/426 |
| 5,797,946 A | 8/1998 | Chin | |
| 5,906,997 A | 5/1999 | Schwartz et al. | |
| 5,932,539 A | 8/1999 | Stupp et al. | |
| 6,005,162 A | 12/1999 | Constantz | |
| 6,034,140 A | 3/2000 | Schwartz et al. | |
| 6,113,640 A | 9/2000 | Tormala et al. | |
| 6,132,668 A | 10/2000 | Baars et al. | |
| 6,133,325 A | 10/2000 | Schwartz et al. | |
| 6,136,333 A * | 10/2000 | Cohn et al. | 424/423 |
| 6,153,252 A | 11/2000 | Hossainey et al. | |
| 6,211,217 B1 * | 4/2001 | Spinale et al. | 514/381 |
| 6,244,868 B1 | 6/2001 | Schappert | |
| 6,280,473 B1 | 8/2001 | Lemperle et al. | |
| 6,315,788 B1 * | 11/2001 | Roby | 605/230 |
| 6,331,312 B1 | 12/2001 | Lee et al. | |
| 6,333,029 B1 | 12/2001 | Vyakarnam et al. | |
| 6,391,059 B1 | 5/2002 | Lemperle et al. | |
| 6,451,373 B1 | 9/2002 | Hossainy et al. | |
| 6,530,956 B1 | 3/2003 | Mansmann | |
| 6,531,146 B2 | 3/2003 | Calhoun et al. | |
| 6,596,267 B1 | 7/2003 | Hubbell et al. | |
| 6,673,362 B2 | 1/2004 | Calhoun et al. | |
| 6,719,795 B1 | 4/2004 | Cornwall et al. | |
| 7,074,239 B1 | 7/2006 | Cornwall et al. | |
| 7,537,782 B2 | 5/2009 | Calhoun et al. | |
| 2001/0004693 A1 | 6/2001 | Burkhead et al. | |
| 2001/0056303 A1 | 12/2001 | Caneiro et al. | |
| 2002/0001609 A1 * | 1/2002 | Calhoun et al. | 424/426 |
| 2002/0173213 A1 | 11/2002 | Chu et al. | |
| 2003/0059463 A1 | 3/2003 | Lahtinen | |
| 2003/0185874 A1 * | 10/2003 | Calhoun et al. | 424/426 |
| 2004/0018175 A1 | 1/2004 | Dimitrijevich | |
| 2004/0030304 A1 | 2/2004 | Hunt et al. | |
| 2005/0074495 A1 | 4/2005 | Schwartz et al. | |
| 2005/0175665 A1 | 8/2005 | Hunter et al. | |
| 2008/0063686 A1 | 3/2008 | Calhoun et al. | |

FOREIGN PATENT DOCUMENTS

EP          0224460 A2      6/1987

(Continued)

OTHER PUBLICATIONS

Maim et al., Prevention of postoperative pericardial adhesions by closure of the pericardium with absorbable polymer patches; The Journal of Thoracic and Cardiovascular Surgery; 104, 3, pp. 600-607, (1992).*

(Continued)

*Primary Examiner*—Robert A. Wax
*Assistant Examiner*—Bethany Barham
(74) *Attorney, Agent, or Firm*—Stout, Uxa, Buyan & Mullins, LLP

(57) ABSTRACT

Resorbable polylactide polymer healing membranes and methods of their applications are disclosed. In a broad embodiment, the invention features methods for inducing proper tissue healing after an open heart surgery. In one embodiment, the methods includes a step of forming a patch with a healing membrane over the open pericardium to induce proper tissue healing and placement in other open heart surgery procedures to facilitate re-entry by the surgeon.

13 Claims, 16 Drawing Sheets

FOREIGN PATENT DOCUMENTS

| | | | |
|---|---|---|---|
| EP | 1384450 | A1 | 1/2004 |
| JP | 7116241 | A | 5/1995 |
| JP | 2000503555 | A | 3/2000 |
| JP | 2000189509 | A | 7/2000 |
| JP | 2000265333 | A | 9/2000 |
| JP | 2003103429 | A | 4/2003 |
| JP | 2007504227 | A | 3/2007 |
| JP | 200833718 | A | 2/2008 |
| JP | 2008300481 | A | 12/2008 |
| WO | 9013302 | | 11/1990 |
| WO | 9317635 | A1 | 9/1993 |
| WO | 9320859 | | 10/1993 |
| WO | 9320859 | A1 | 10/1993 |
| WO | 9951163 | | 10/1999 |
| WO | 0015270 | A1 | 3/2000 |
| WO | 0015273 | A1 | 3/2000 |
| WO | 0062707 | | 10/2000 |
| WO | 0167987 | | 9/2001 |
| WO | 0167987 | A1 | 9/2001 |

OTHER PUBLICATIONS

Definition of "mil". Online. Accessed on Aug. 22, 2006. <http://rel.intersil.com/docs/lexicon/M.html>. p. 3 of 6.*

Supplementary European Search Report from application No. EP 03772191, mailed Aug. 31, 2009.
Supplementary European Search Report from application No. EP 05786506, mailed Sep. 10, 2009.
International Search Report and Written Opinion from application No. PCT/US09/49728, mailed Aug. 19, 2009.
International Search Report, Jun. 6, 2001, PCT/US01/07989.
International Search Report, Jan. 11, 2005, PCT/US03/23919.
International Search Report, Jan. 11, 2005, PCT/US03/24824.
International Search Report, Mar. 2, 2006, PCT/US05/28834.
Casey K. Lee et al. "Prevention of Postlaminectomy Scar Formation" Spine, vol. 9, No. 3, 1984, p. 305-312.
Maglio G et al. "Compatibilized poly (Epsilon-Caprolactone)/Poly(L-Lactide) Blends for Biomedical Uses" Macromol, Rapid Commun 20 No. 4, p. 236-238 (1999).
Dieter Bendix "Chemical synthesis of polylactide and its copolymers for medical applications" Polymer Degradation and Stability 59 (1998) p. 129-135.
Gates, Kimberly "Controlled Drug Delivery Using Bioerodible Polymeric Systems for the Treatment of Periodontitis" Graduate Department of Pharmaceutical Sciences, University of Toronto (1999), printed pp. 1-173, especially p. 56.

* cited by examiner

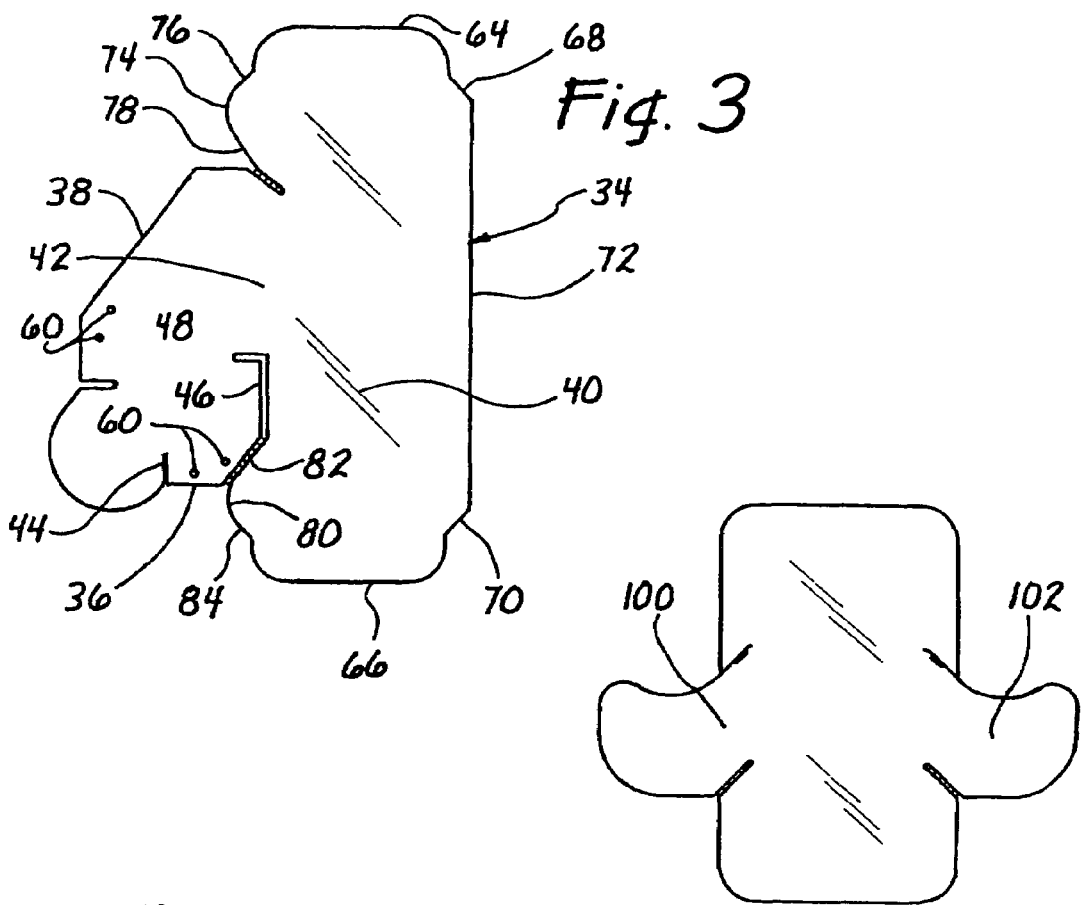
Fig. 3
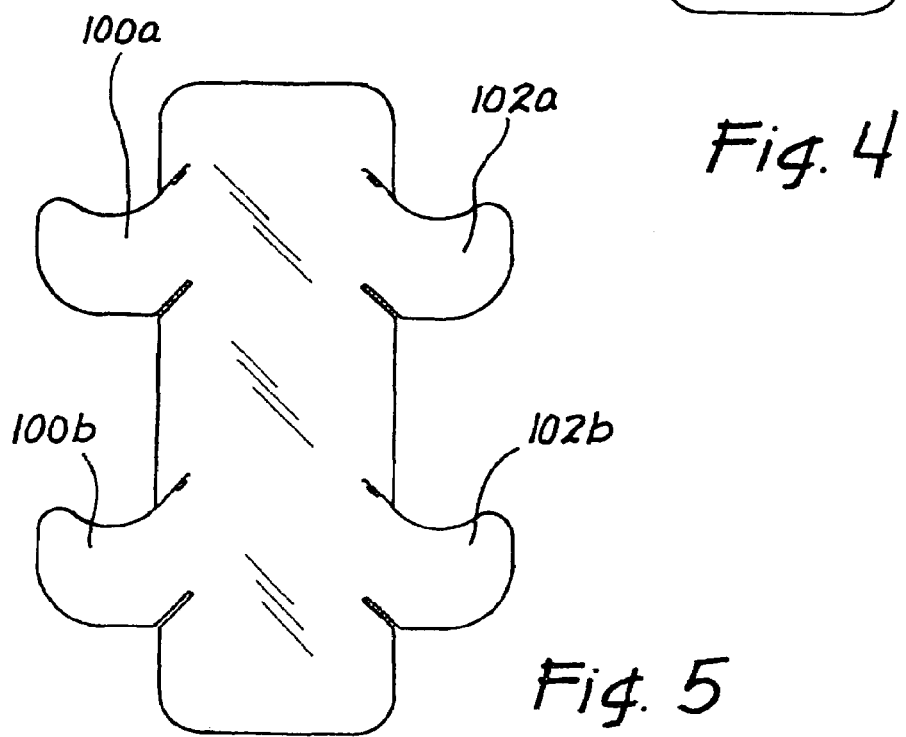
Fig. 4
Fig. 5

Fig. 10a
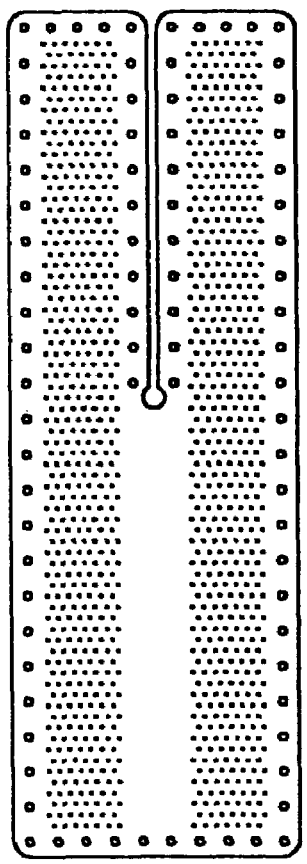
Fig. 10b
Fig. 11a
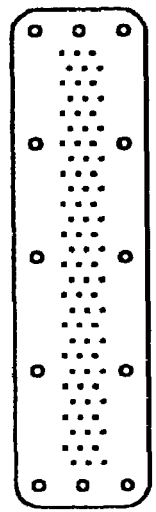
Fig. 11b

Fig. 15a
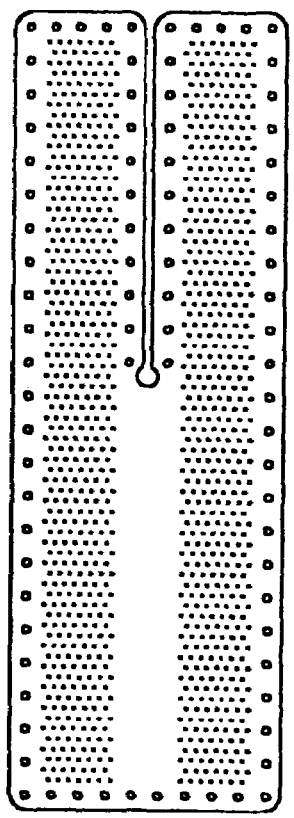
Fig. 15b
Fig. 16a
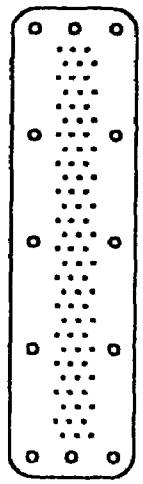
Fig. 16b

METHODS OF PROMOTING ENHANCED HEALING OF TISSUES AFTER CARDIAC SURGERY

CROSS-REFERENCE TO RELATED APPLICATIONS

This application claims the benefit of U.S. Provisional Application No. 60/429,166, filed Nov. 25, 2002, and U.S. Provisional Application No. 60/409,459, filed Sep. 10, 2002, the contents of which in their entireties are hereby incorporated by reference.

BACKGROUND OF THE INVENTION

1. Field of the Invention

The present invention relates generally to medical devices and, more particularly, to methods of applying the medical device for inducing proper healing of tissues, for example the parietal pericardium tissue, after a cardiac surgery.

2. Description of Related Art

The formation of excessive amounts of fibrotic or scar tissue (fibrosis) is a central issue in medicine. Scar tissue can block arteries, immobilize joints, damage internal organs, and can in some instances generally impede a body's ability to maintain vital functions. Every year, about 1.3 million people are hospitalized due to the damaging effects of fibrosis, yet doctors have few optimal remedies To help them control this dangerous condition. Fibrosis can follow surgery in the form of adhesions, keloid tumors or hypertrophic (very severe) scarring. Fibrotic growth can also proliferate and invade the healthy tissue that surrounds it, even after the original injury heals. Too much scar tissue may cause physiological roadblocks that disfigure, cripple or even kill.

One of the most important pathologies in which fibrosis is problematic is cardiac surgery. The number of patients undergoing cardiac surgery has been steadily increasing, and as a consequence, the number of cardiac reoperations has also increased. It has been estimated that one out of every five patients undergoing coronary artery bypass surgery will require a reoperation. Reoperative cardiac surgical procedures can be associated with an even significantly greater complication rate than that of the initial procedure. For example, the post-operative complication rate following a reoperative coronary artery bypass procedure can be double. As a consequence, cardiac reoperations can introduce increased risks of morbidity and mortality. An important contributory factor for the increased complications with cardiac reoperations is the adhesions which form secondarily from the initial entry into the pericardium. These fibrous adhesions can begin to form immediately following the surgical procedure and can consist of collagen and other extra cellular proteins.

There is a need for improved methods of inducing proper tissue healing, e.g. healing without adhesion, for tissues affected by an open heart surgery.

SUMMARY OF THE INVENTION

The present invention provides resorbable thin membranes for use in promoting healing of tissues affected by an open heart surgery, and methods for using same. In one embodiment, the methods comprise using a healing membrane to form a patch over a ruptured tissue to induce proper healing of that tissue. In another embodiment, the methods comprise inserting a healing membrane between tissues which may scar or adhere to each other to induce proper healing, i.e. to prevent such scaring or adhesion.

The healing membranes are preferably constructed from a resorbable polylactide polymer, and can be formed to have thicknesses on the order of microns, such as, for example, thicknesses between 10 and 300 microns. The healing membranes can be preshaped with welding flanges and stored in sterile packaging.

Any feature or combination of features described herein are included within the scope of the present invention provided that the features included in any such combination are not mutually inconsistent as will be apparent from the context, this specification, and the knowledge of one of ordinary skill in the art. In addition, any feature or combination of features may be specifically excluded from any embodiment of the present invention. Additional advantages and aspects of the present invention are apparent in the following detailed description and claims.

BRIEF DESCRIPTION OF THE DRAWINGS

FIG. 2b is an enlarged view of FIG. 2a;

FIG. 3 illustrates a scar-reduction resorbable healing membrane for application to the exiting nerve root of the spinal chord in accordance with a first pre-formed embodiment of the present invention;

FIG. 4 illustrates a scar-reduction resorbable healing membrane for application to two exiting nerve roots of the spinal chord in accordance with a second pre-formed embodiment of the present invention;

FIG. 5 illustrates a scar-reduction resorbable healing membrane for application to four exiting nerve roots of the spinal chord in accordance with a third pre-formed embodiment of the present invention;

FIG. 6a is a top planar view of a scar-reduction resorbable healing membrane in accordance with a fourth pre-formed embodiment of the present invention;

FIG. 6b is a cross-sectional view of the scar-reduction resorbable healing membrane shown in FIG. 6a;

FIG. 7a is a top planar view of a scar-reduction resorbable healing membrane in accordance with a fifth pre-formed embodiment of the present invention;

FIG. 7b is a cross-sectional view of the scar-reduction resorbable healing membrane shown in FIG. 7a;

FIG. 8b is a cross-sectional view of the scar-reduction resorbable healing membrane shown in FIG. 8a;

FIG. 9a is a top planar view of a scar-reduction resorbable healing membrane in accordance with a seventh pre-formed embodiment of the present invention;

FIG. 9b is a cross-sectional view of the scar-reduction resorbable healing membrane shown in FIG. 9a;

FIG. 10a is a top planar view of a scar-reduction resorbable healing membrane in accordance with an eighth pre-formed embodiment of the present invention;

FIG. 10b is a cross-sectional view of the scar-reduction resorbable healing membrane shown in FIG. 10a;

FIG. 11a is a top planar view of a scar-reduction resorbable healing membrane in accordance with a ninth pre-formed embodiment of the present invention;

FIG. 11b is a cross-sectional view of the scar-reduction resorbable healing membrane shown in FIG. 11a;

FIG. 12a is a top planar view of a scar-reduction resorbable healing membrane in accordance with a tenth pre-formed embodiment of the present invention;

FIG. 12b is a cross-sectional view of the scar-reduction resorbable healing membrane shown in FIG. 12a;

FIG. 13b is a cross-sectional view of the scar-reduction resorbable healing membrane shown in FIG. 13a;

FIG. 14b is a cross-sectional view of the scar-reduction resorbable healing membrane shown in FIG. 14a;

FIG. 15a is a top planar view of a scar-reduction resorbable healing membrane in accordance with a thirteenth pre-formed embodiment of the present invention;

FIG. 15b is a cross-sectional view of the scar-reduction resorbable healing membrane shown in FIG. 15a;

FIG. 16a is a top planar view of a scar-reduction resorbable healing membrane in accordance with a fourteenth pre-formed embodiment of the present invention;

FIG. 16b is a cross-sectional view of the scar-reduction resorbable healing membrane shown in FIG. 16a;

FIG. 17b is a cross-sectional view of the scar-reduction resorbable healing membrane shown in FIG. 17a.

DESCRIPTION OF THE PRESENTLY PREFERRED EMBODIMENTS

Figure 1A:
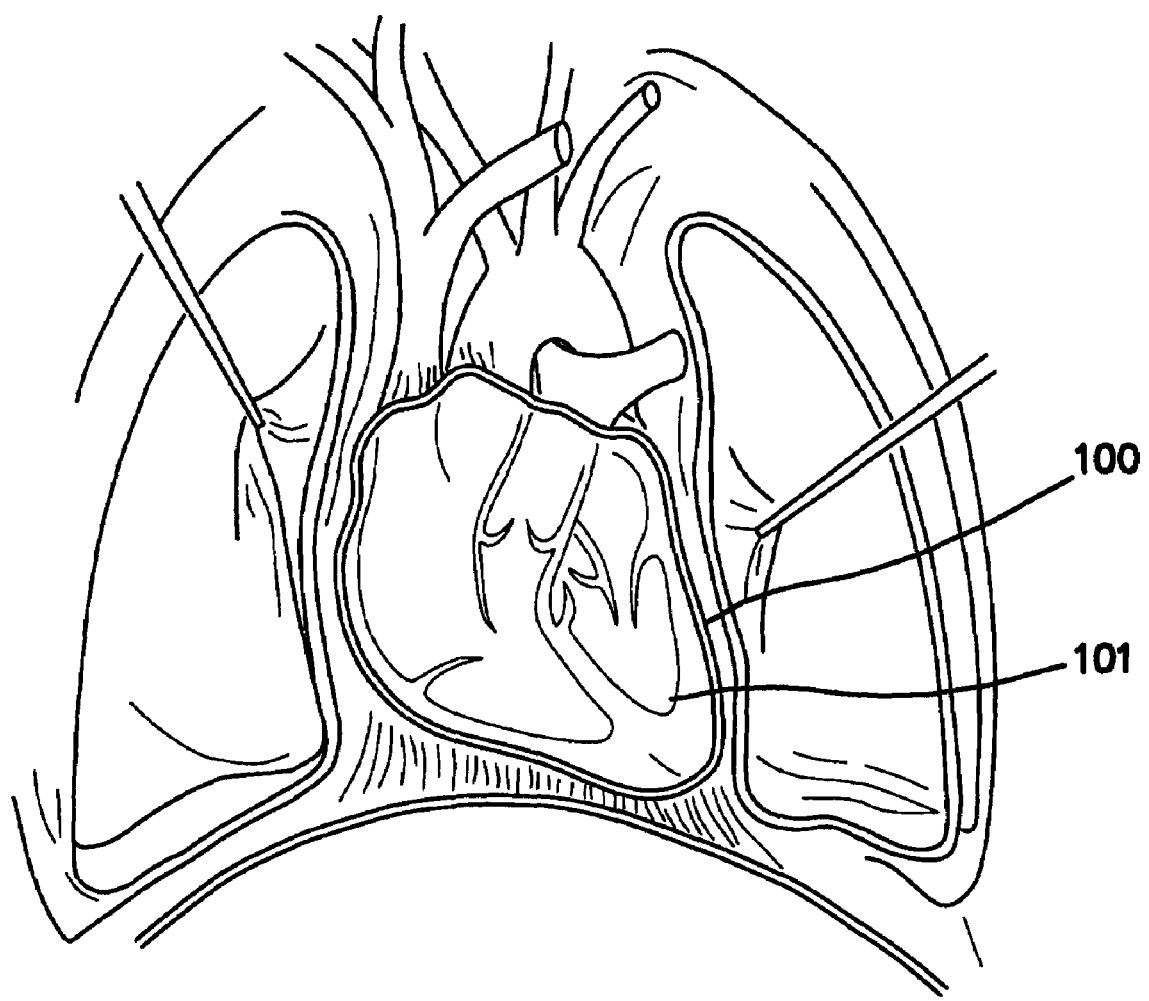
FIG. 1a shows a frontal coronal sectional view of a human chest.

Reference will now be made in detail to the presently preferred embodiments of the to invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims.

It is to be understood and appreciated that the process, steps and structures described herein do not cover a complete process flow for the attenuation of scar tissue formation during an open heart surgical procedure. The present invention may be practiced in conjunction with various cardiac surgical techniques that are conventionally used in the art, and only so much of the commonly practiced process steps are included herein as are necessary to provide an understanding of the present invention.

The present invention provides resorbable implants in the form of healing membranes that can be used in various surgical contexts, including applications wherein the healing membranes are implemented to induce proper healing of tissues injured or subject to injury as a result of a surgical procedure, such as an open heart surgical procedure.

Injured tissues can include tissues that are ruptured or damaged. These injured tissues may not properly anneal, may scar, and/or may adhere to other tissues. Tissues which could potentially be damaged by open heart surgical procedures are those tissues which are not injured themselves but which are susceptible to being affected by injured tissues. For example, such tissues may adhere to injured tissues.

Generally, an inducement of healing tissues includes an inducement for ruptured (e.g., severed) tissues to anneal and injured tissues to return to substantially normal states. In one embodiment, the inducement of proper healing of tissues includes inducing an annealing of a ruptured tissue, such as a ruptured pericardial tissue. Preferably, the annealing of the tissue in accordance with the invention is with reduced or eliminated scaring of the annealing tissue and/or surrounding tissues. In one embodiment, the inducing of proper healing of tissues also includes the inducing of healing of tissues of different types, for example heart tissue, pericardial tissue and bone (sternum) tissue, with reduced or eliminated scaring or adhesion to one other. For example, the methods of the present invention can facilitate the pericardium to heal with little or no adhering to the heart or the sternum. Furthermore, the methods of the present invention can allow for the sternum and the heart to heal with little or no adherence therebetween.

Figure 1B:
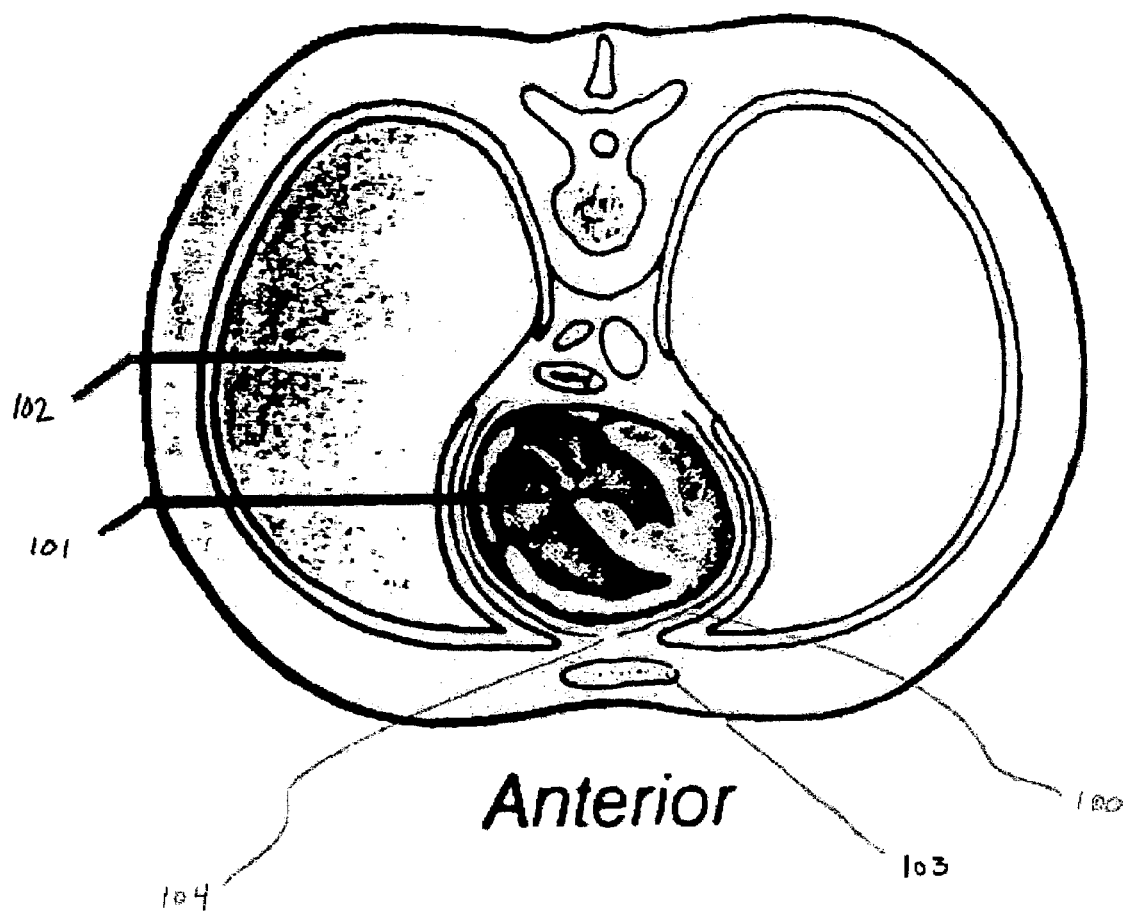
FIG. 1b shows a transverse sectional view of a human chest region.

Referring to FIG. 1a, a frontal coronal cross section of a human chest is illustrated. The heart 101 is encased in a parietal pericardium (pericardial tissue) 100. FIG. 1b is a transverse cross section of a human chest showing the heart 101 being encased in a pericardium 100. The pericardium provides a region between the heart 101 and other non-heart tissues, such as tissues of the lung 102 and the sternum 103. In an open heart surgery, the sternum 103 and the pericardium 100 are typically severed. In an open heart surgery, the severed pericardium 100 creates an open section 104 which provides the surgeon with direct access to the heart.

Figure 1C:
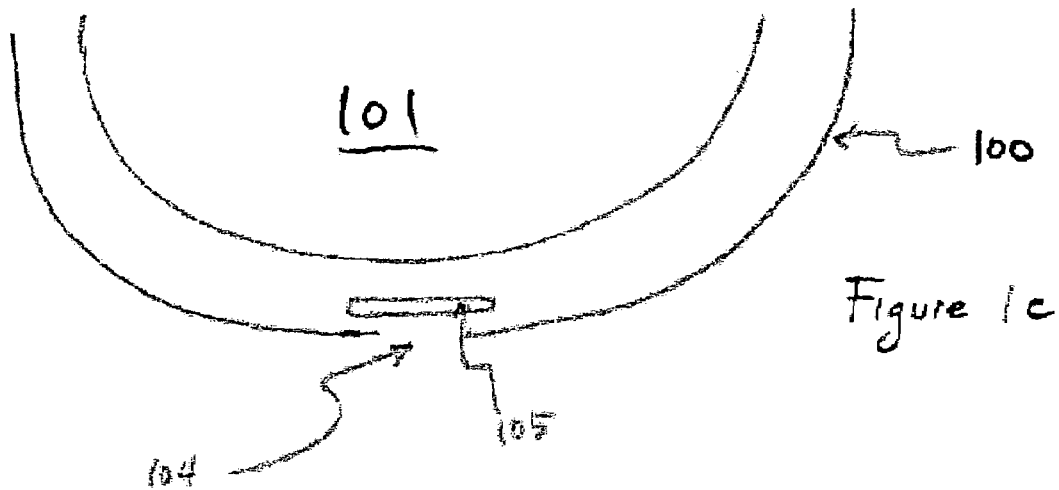
FIGS. 1c through 1e show an enlarged transverse sectional view of the heart and the pericardium.
Figure 1D:
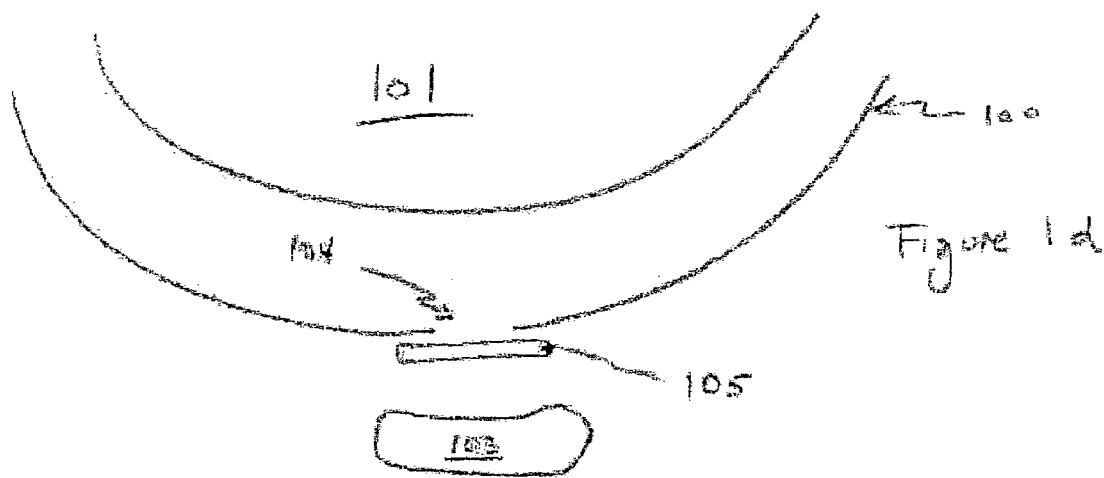
Figure 1E:
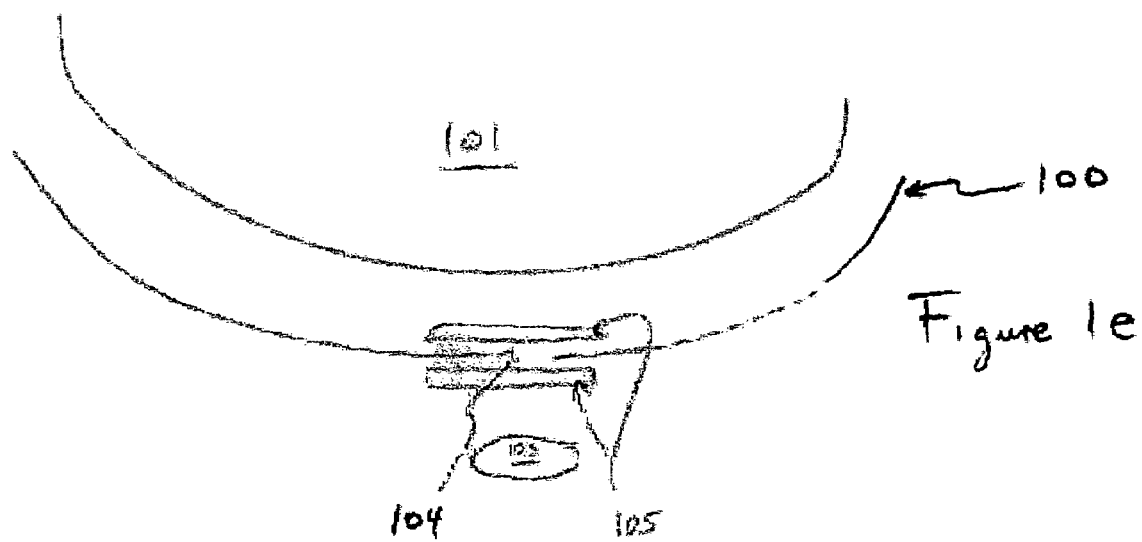

FIGS. 1c through 1e are enlarged transverse cross sections of a human chest, focusing at the region where the pericardium 100 is severed. These figures show a healing membrane 105 forming a patch over the open section 104 of the pericardium 100 after a cardiac operation is completed. Preferably, placing a patch over the open sections 104 may act as a scaffold for the ruptured pericardium 100 to regenerate and heal. For example, the patch may provide a substrate for the pericardial tissue 100 to attach to and grow over as the tissue heals. In certain embodiments, the pericardial tissue attaches directly to the patch. In other embodiments, a tissue attachment component may be provided on the patch so that the tissue can attach to the tissue attachment component. For example, a healing membrane may include one or more regions with a extracellular matrix protein component, such as a fibrin component, provided in an amount to facilitate tissue regeneration over the membrane.

FIG. 1c shows an embodiment where the healing membrane 105 is positioned between the heart 101 and the pericardium 100. Preferably, the healing membrane 105 allows for the ruptured pericardium 100 to anneal without adhering to the heart. The healing membrane 105, which may comprise a resorbable thin membrane such as described below, is preferably sized to have a surface area that is larger than an area of the open section 104. The healing membrane 105 is folded, rolled or otherwise reduced in size, and then inserted through the open section 104. Subsequently, the healing membrane 105 is positioned between the heart 101 and edges of the open section 104 into a position and orientation as shown. FIG. 1d shows an embodiment where the healing membrane 105 is positioned between the pericardium 100 and the sternum 103. Preferably, the healing membrane 105 allows for the ruptured pericardium 100 to anneal without adhering to the sternum 103. FIG. 1e shows an embodiment where the pericardium 100 is sandwiched between two healing membranes 105. Preferably, this arrangement allows for the ruptured pericardium 100 to anneal without adhering to the heart and the sternum.

In one embodiment, the healing membranes may be attached to the pericardium. In another embodiment, one of the healing membranes may be attached to the sternum. For example, in FIGS. 1d and 1e, the healing membranes 105 positioned between the pericardium 100 and the sternum 103 may be attached to the sternum. The attachment of the healing membrane to the pericardium and/or sternum may be achieved using a securing technique such as discussed below. For example, in one embodiment the healing membrane is heat welded, and in other embodiments, the healing membrane or membranes may be sutured, clamped, glued or otherwise physically mounted to the pericardium and/or the sternum. In addition, when two or more healing membranes are used in a surgical procedure, the healing membranes may be secured to each other.

Figure 1F:
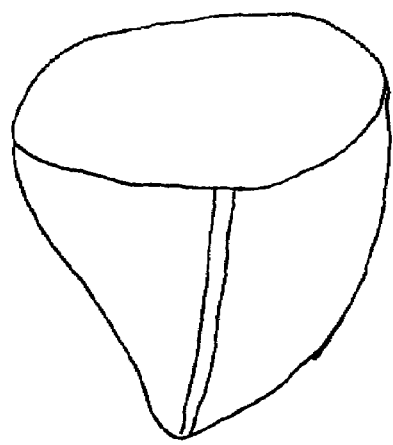
FIG. 1f shows a resorbable healing membrane precontoured into a heart-shaped bag.

In another embodiment, a precontoured bag in the form of the apex of the heart is placed between the pericardium and the heart. FIG. 1f shows a resorbable healing membrane precontoured into a heart-shaped full or partial enclosure or bag. For example, the resorbable healing membrane can be precontoured into a heart-shaped bag to surround the apex of a heart. The precontoured resorbable healing membrane is shown having an optional slit to facilitate placement.

Mediastinal adhesions can also occur as a result of an open heart surgery. In one embodiment, a healing membrane may be placed between the tissues where such adhesions are likely to occur to prevent adhesion. An advantage to practicing the methods of the present invention is that the placement of the healing membrane between the tissues may prevent scaring and create a dissection plane. For patients undergoing a second surgical cardiac procedure, the dissection plane can allow a surgeon to re-enter the previous operation site without having to cut through scar tissue, thereby reducing operation time and potential complications (e.g., damage to the heart and vessels).

The healing membranes used in practicing the methods of the present invention can include polylactide polymers and/or co-polymers. The resorbable healing membrane of the present invention is preferably smooth and non-porous. Moreover, the healing membrane is preferably bioabsorbable in the body. In one embodiment, the healing membrane material comprises about 60% to about 80% of a polylactide polymer, and about 20% to about 40% of a co-polymer. For example, a healing membrane may comprise poly (L-lactide-co-D,L-lactide) 70:30 Resomer LR708 manufactured and supplied from Boehringer Ingelheim KG of Germany. In one embodiment, the healing membrane has an intrinsic viscosity of about 3 to about 7, preferably about 3.5. In another embodiment, the polylactide has additional copolymers of poly caprolactone or trimethylene carbonate to increase the compliance or flexibility of the film. In this embodiment, the healing membrane material can comprise about 60% to about 80% of a polylactide polymer, and about 20% to about 40% of the co-polymer (caprolactone and/or trimethylene carbonate).

A pre-formed healing membrane made from the material can be shaped at the time of surgery by bringing the material to its glass transition temperature, using heating iron, hot air, heated sponge or hot water bath methods. The scar-tissue reduction healing membrane of the present invention preferably has a uniform thickness of less than about 300 microns, preferably less than 200 microns, and more preferably between 10 microns and 100 microns. As defined herein, the "healing membranes" of the present invention comprise thicknesses between 10 microns and 300 microns and, preferably, between 10 and 100 microns.

In one embodiment, the healing membrane comprises two opposing surfaces. On one side of the healing membrane, there is a substantially-smooth surface, and optionally on the other side there is also a substantially-smooth surface. In certain embodiments, one surface may include a non-smooth surface that facilitates tissue growth while minimizing scarring. For example, the surface may include one or more regions containing indentations, protrusions, and/or irregular roughened patterns that are effective to promote tissue growth without causing substantial tissue scarring.

In one embodiment, the healing membrane may also serve as a barrier membrane. As such, the healing membrane may be provided in any shape which may effectively serve as a barrier between two different types of tissues, for example heart tissue and pericardium tissue. In one embodiment, the healing membrane material may be provided in rectangular shapes that are, for example, several centimeters on each side (e.g., between about 2 centimeters and about 10 centimeters or more), or can be cut and formed into specific shapes, configurations and sizes by the manufacturer before packaging and sterilization. The thin healing membranes of the present invention are sufficiently flexible to conform around anatomical structures, although some heating in a hot water bath may be desirable for thicker configurations. In modified embodiments, certain polylactides which become somewhat more rigid and brittle at thicknesses above 0.25 mm and which can be softened by formation with a copolymer and another polylactide, for example, may be implemented to form scar-reduction resorbable barrier micro-healing membrane.

Figure 1G:
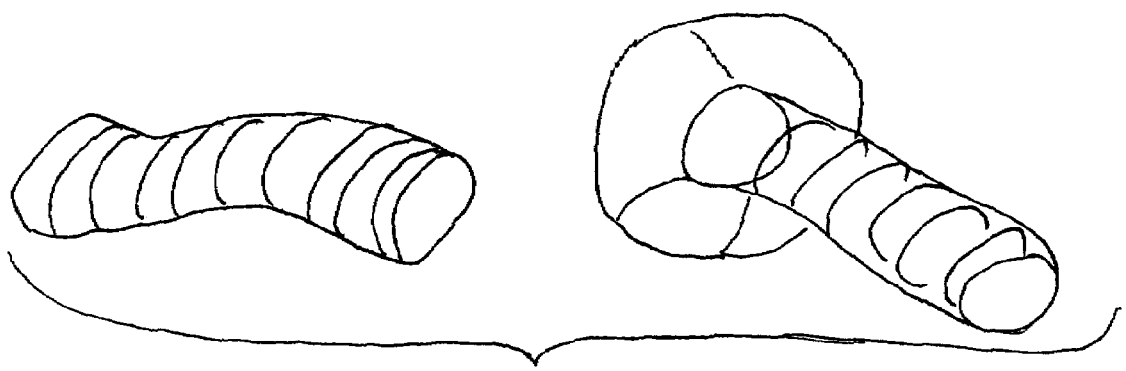
FIG. 1g shows a resorbable healing membrane precontoured into tubes for covering the conduits of a left ventricular assist device.
Figure 1H:
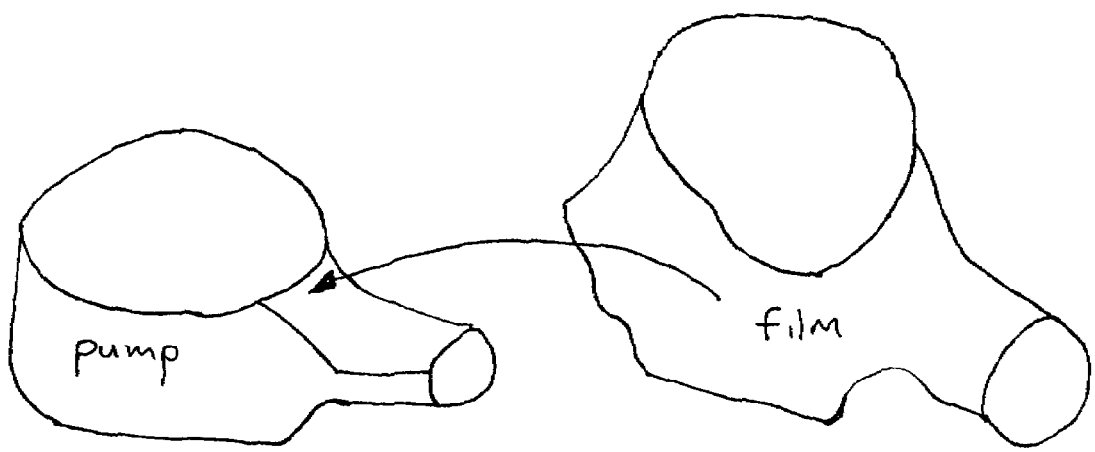
FIG. 1h shows a resorbable healing membrane precontoured to accommodate the pumps of a left ventricular assist device.

In further embodiments, the film is precontoured into forms such as pumps or conduits to add in the reoperation of left ventricular assist devices (LVAD). FIG. 1g shows two resorbable healing membranes precontoured into tubes for covering the conduits of a LVAD. One of the two precontoured resorbable healing membranes comprises a cylindrical shape and the other of the two exemplary precontoured resorbable healing membranes comprises an enlarged flange for coupling to a pump. Either of the two precontoured resorbable healing membranes may have optional slits, running along lengths thereof, for example, to facilitate placement over a conduit. FIG. 1h shows a resorbable healing membrane precontoured to accommodate the pumps of a LVAD. The precontoured forms can facilitate placement of the scar-reduction membrane, can reduce the displacement of the scar-reducing membrane after closure of the wound, and can facilitate re-entry by the surgeon by controlling the adhesions from attaching to the LVAD hardware.

In one embodiment, the healing membranes of the present invention are impregnated with a therapeutically effective amount of an anti-scar forming agent. Angiotensin antagonists have been found to reduce tissue scar formation. See, for example, U.S. Pat. No. 6,211,217, the disclosure of which is incorporated in its entirety herein by reference. Thus, in a preferred embodiment, the healing membranes are impregnated with an angiotensin antagonist. Without wishing to limit the invention to any theory or operation, it is believed that the present healing membrane resorbs and advantageously releases the anti-scar forming agent into the surrounding tissue.

The very thin construction of these healing membranes is believed to substantially accelerate the rate of absorption of the implants, compared to rates of absorption of thicker healing membrane implants of the same material. It is believed, however, that resorption into the body too quickly of the healing membrane will yield undesirable drops in local pH levels, thus introducing/elevating, for example, local inflammation, discomfort and/or foreign antibody responses. Further, a resulting uneven (e.g., cracked, broken, roughened or flaked) surface of a healing membrane degrading too early may undesirably cause tissue turbulence between the tissues before, for example, adequate healing has occurred, resulting in potential tissue inflammation and scarring. It is believed that a healing membrane of the present invention having a thickness of about 200 microns or less should maintain its structural integrity for a period in excess of three weeks and, more preferably for at least 7 weeks, before substantially degrading, so that the anti-scarring function can be achieved and optimized. To the extent the healing membrane does not degrade at an accelerated rate, compared to a thicker healing membrane of the same material, the healing membrane should maintain its structural integrity for a period in excess of 6 months and, more preferably for at least one year, before substantially degrading, in order to achieve and optimize the anti-scarring function. The polylactide resorbable polymer healing membranes in accordance with this aspect of the present invention are thus designed to resorb into the body at a relatively slow rate.

As used herein, the term "non-porous" refers to a material which is generally water tight and, in accordance with a preferred embodiment, not fluid permeable. However, in a modified embodiment of the invention, micro-pores (i.e., fluid permeable but not cell permeable) may exist in the resorbable healing membrane of the present invention, to the extent, for example, that they do not substantially disrupt the smoothness of the surfaces of the resorbable healing membrane to cause scarring of tissue. In substantially modified embodiments for limited applications, pores which are cell permeable but not vessel permeable may be manufactured and used. As presently preferred, the resorbable healing membrane is manufactured using a press molding procedure to yield a substantially non-porous film. The healing membrane materials of the present invention may have a semi-rigid construction, and are fully contourable when heated to approximately 55 degrees Celsius. As presently embodied, many of the thinner healing membrane thicknesses can be sufficiently contoured even in the absence of heating.

The non-porosity and the smoothness of the healing membrane can reduce tissue turbulence, enhance tissue guidance, and minimize scar formation. Moreover, the smooth, uninterrupted surface of the healing membrane material may facilitate movement of the local tissues across the area, hence reducing frictional rubbing and wearing which may induce scar tissue formation.

Although the healing membranes are very effective to prevent postoperative mediastinal and pericardial adhesions, these membranes may be used in other surgical applications. For to example, there is evidence pointing to epidural adhesions as possible factors contributing to failed back surgery. Epidural fibrosis may occur following spinal injuries or as a post-operative surgical complication. The dense scar formation on dura and around nerve roots has previously been described as the "laminotomy healing membrane," and has been implicated in rendering subsequent spine operations technically more difficult. In a laminectomy procedure, for example, the scar-reduction resorbable healing membrane of the present invention is desirably inserted between the dural sleeve and the paravertebral musculature post laminotomy and conforms readily to block exposed marrow elements of the laminae. Imposition of the healing membrane material as a barrier between the paravertebral musculature and the epidural space is believed to reduce cellular trafficking and vascular invasion into the epidural space from the overlying muscle and adjacent exposed cancellous bone. Moreover, tests have shown that the present healing membrane material does not appear to interfere with normal posterior wound healing while at the same time inhibiting the unwanted adhesions and scarring.

Figure 2A:
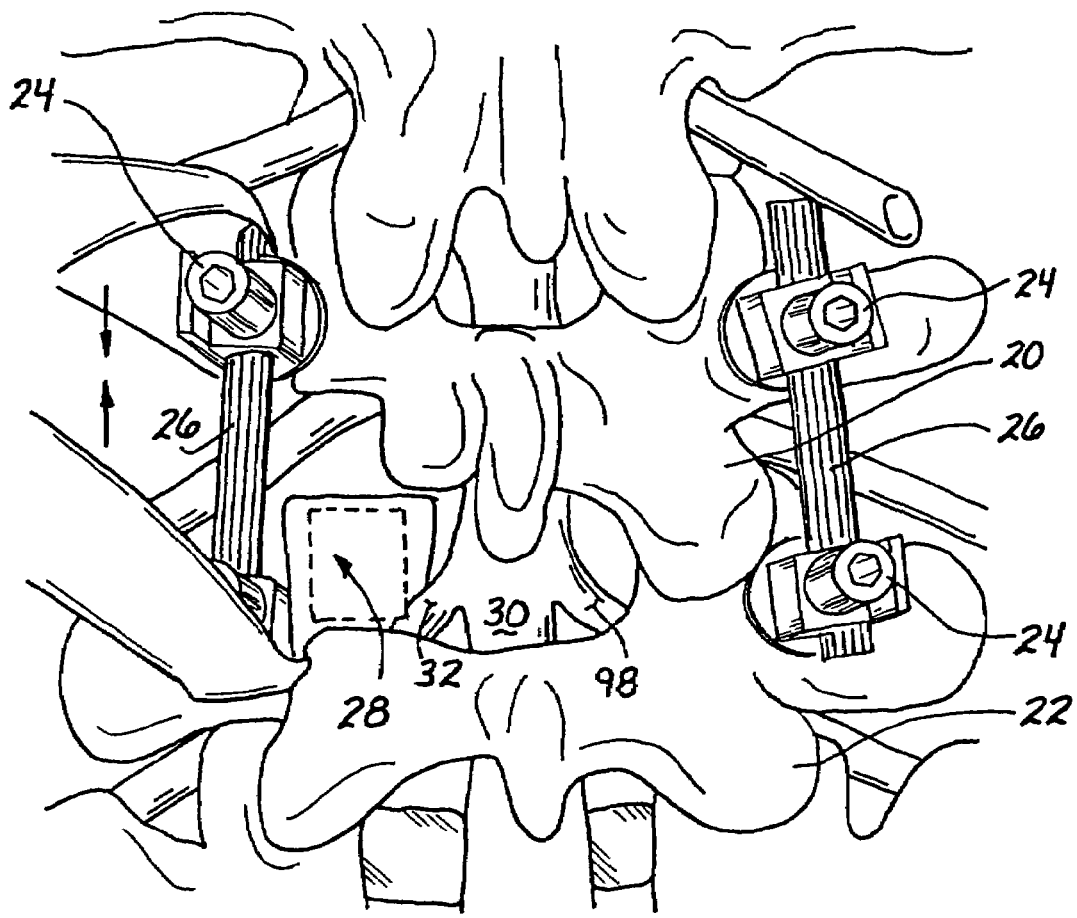
FIG. 2a illustrates a laminotomy procedure wherein a portion of the posterior arch (lamina) of a vertebra is surgically removed.
Figure 2B:
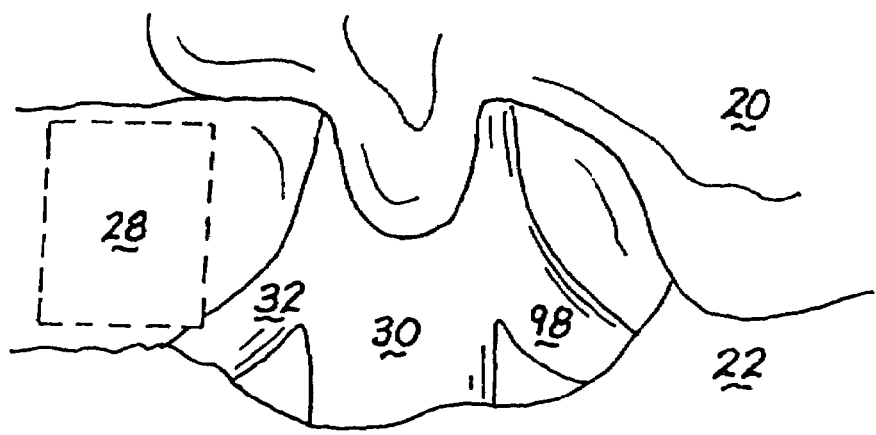
Figures 7A, 7B:
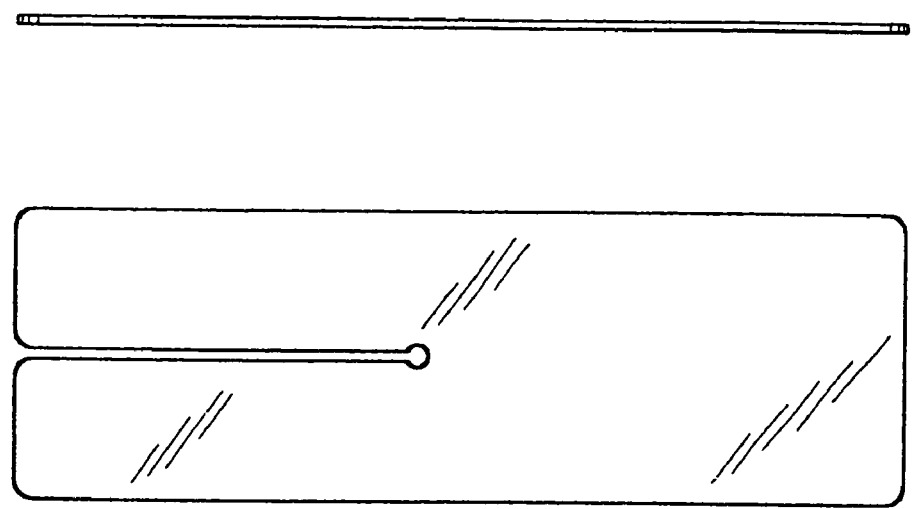
Figures 6A, 6B:
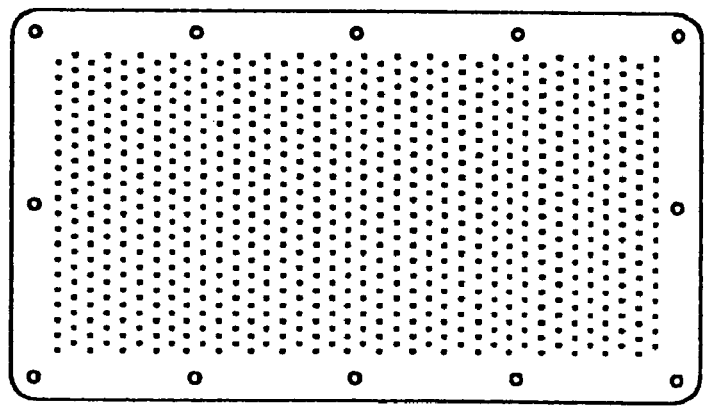
Figure 8B:
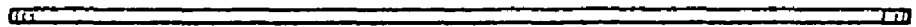
Figure 8A:
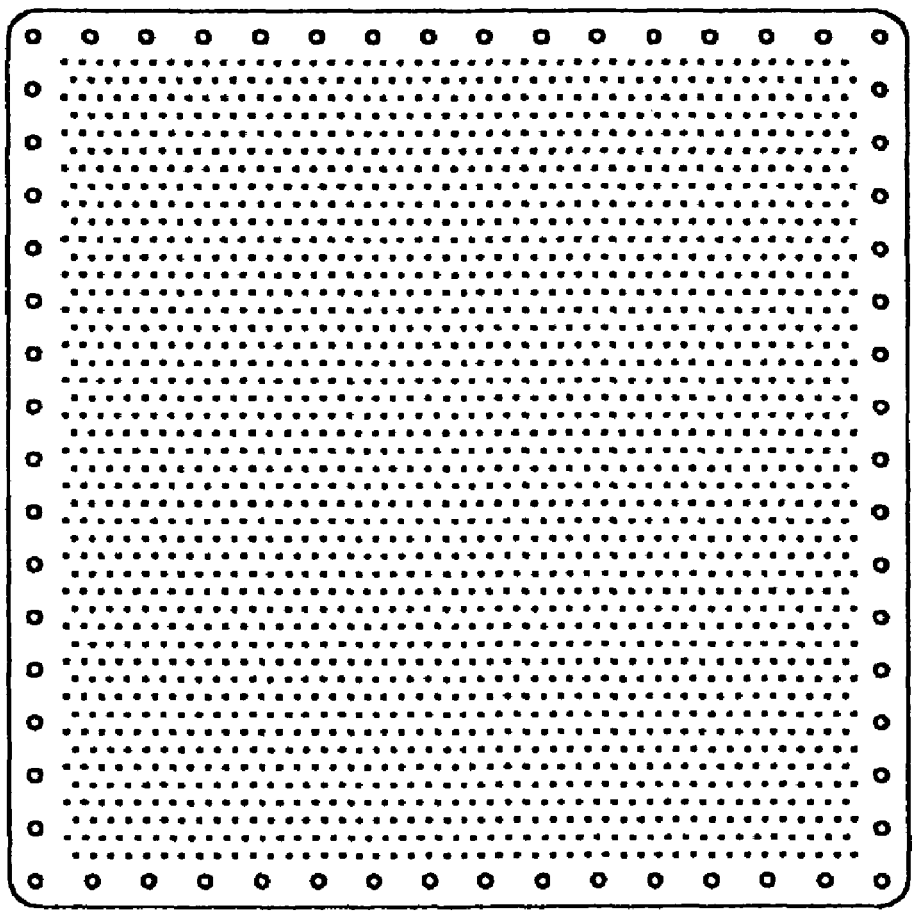
FIG. 8a is a top planar view of a scar-reduction resorbable healing membrane in accordance with a sixth pre-formed embodiment of the present invention.
Figures 9A, 9B:
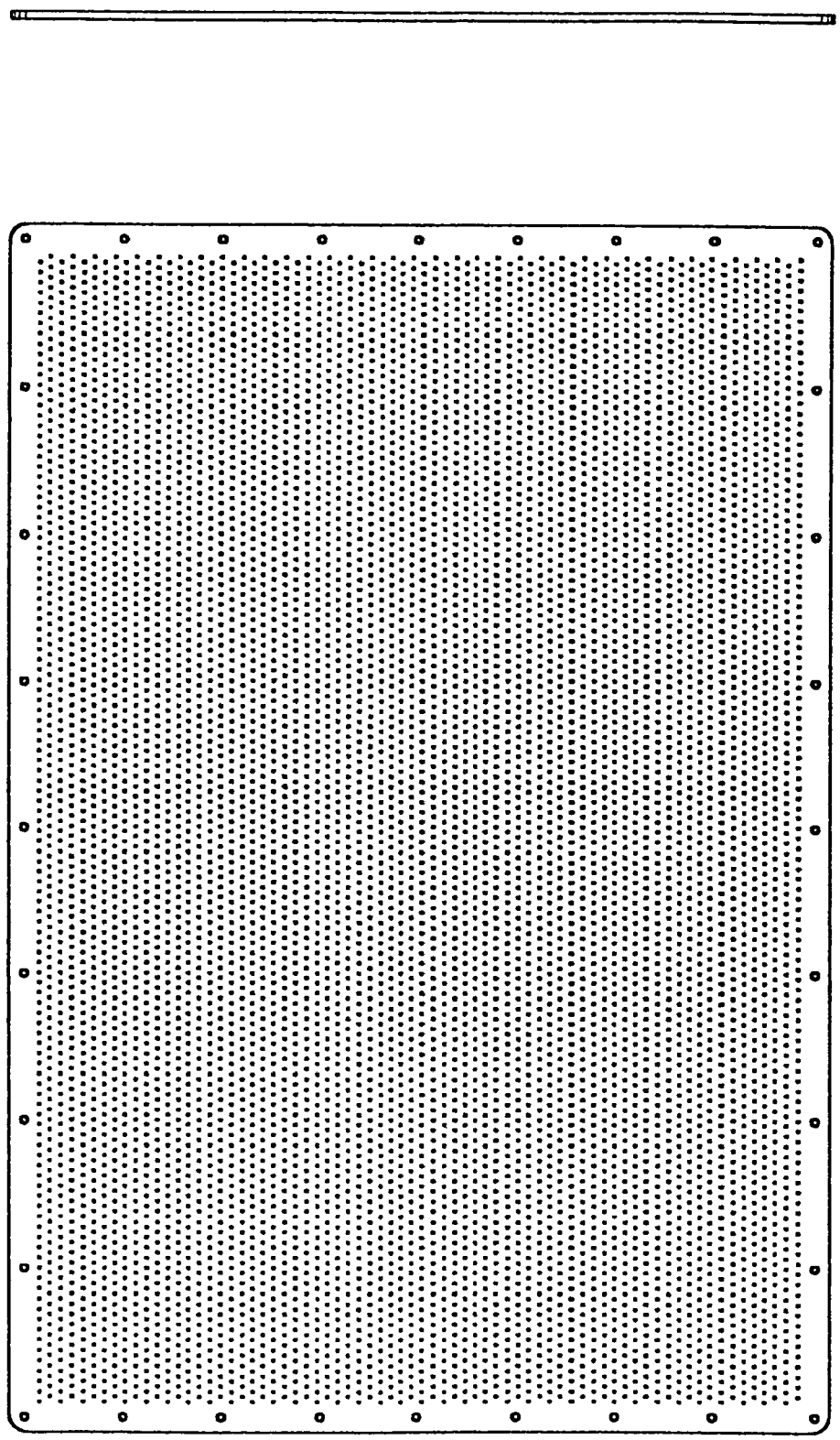
Figures 12A, 12B:
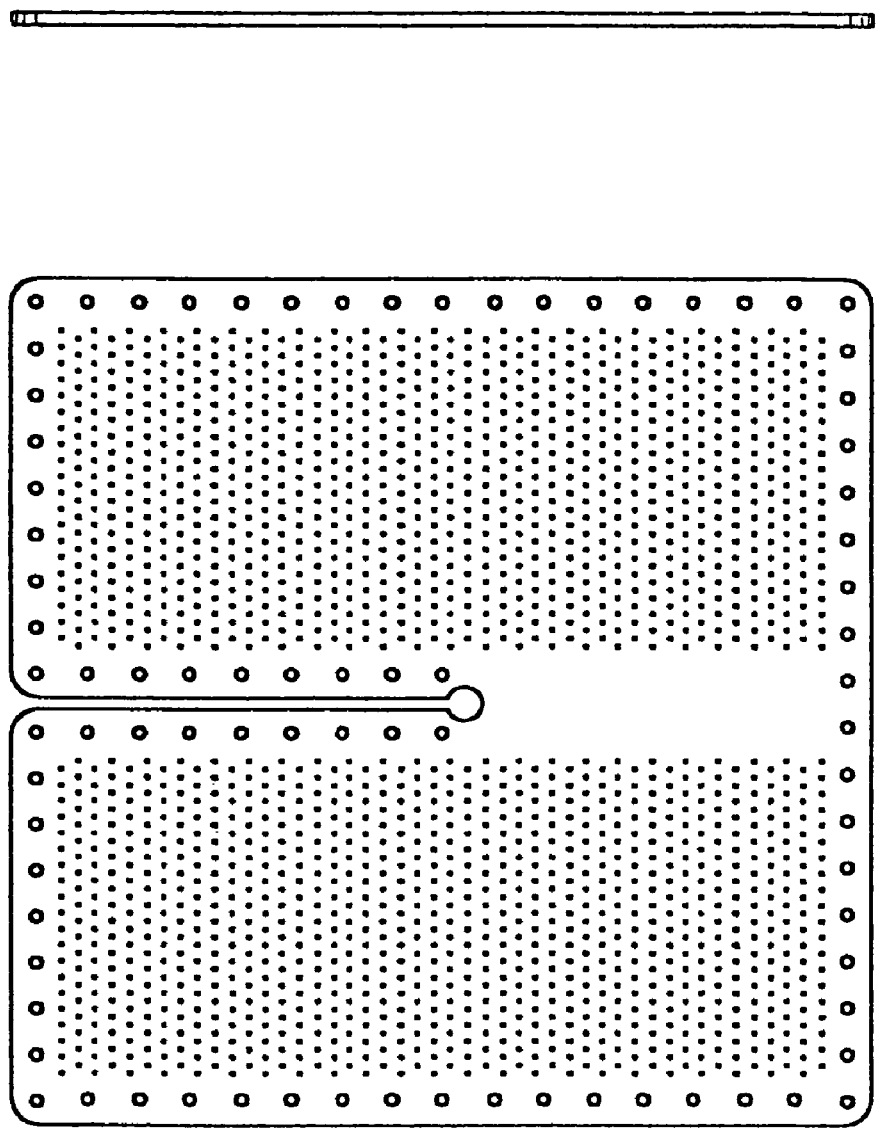
Figure 13A:
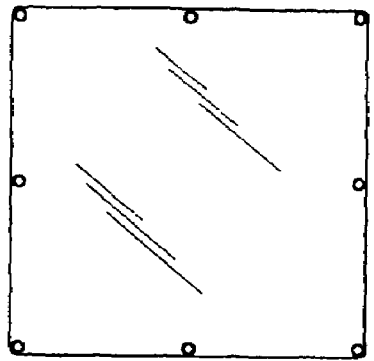
FIG. 13a is a top planar view of a scar-reduction resorbable healing membrane in accordance with an eleventh pre-formed embodiment of the present invention.
Figure 13B:
Figure 14A:
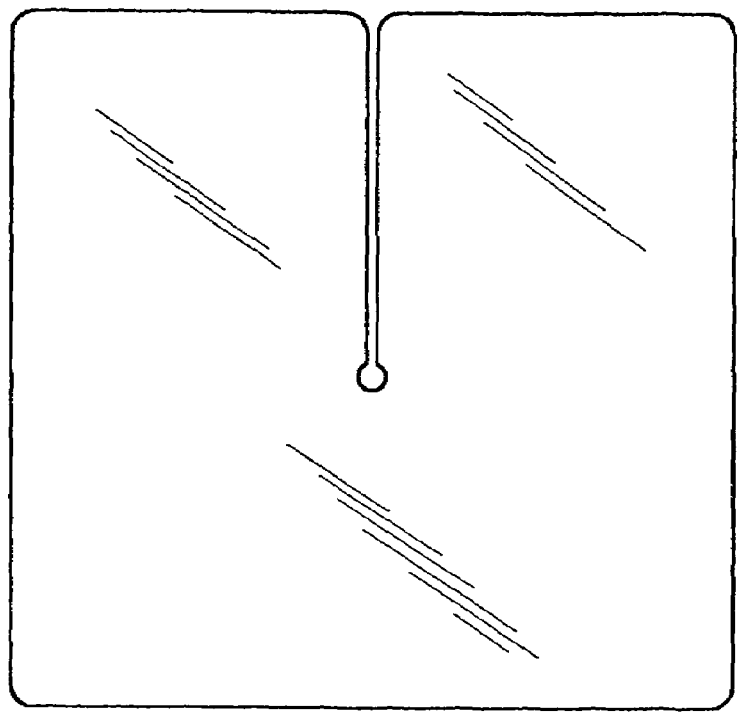
FIG. 14a is a top planar view of a scar-reduction resorbable healing membrane in accordance with a twelfth pre-formed embodiment of the present invention.
Figure 14B:
Figure 17B:
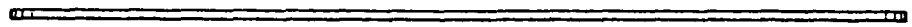
Figure 17A:
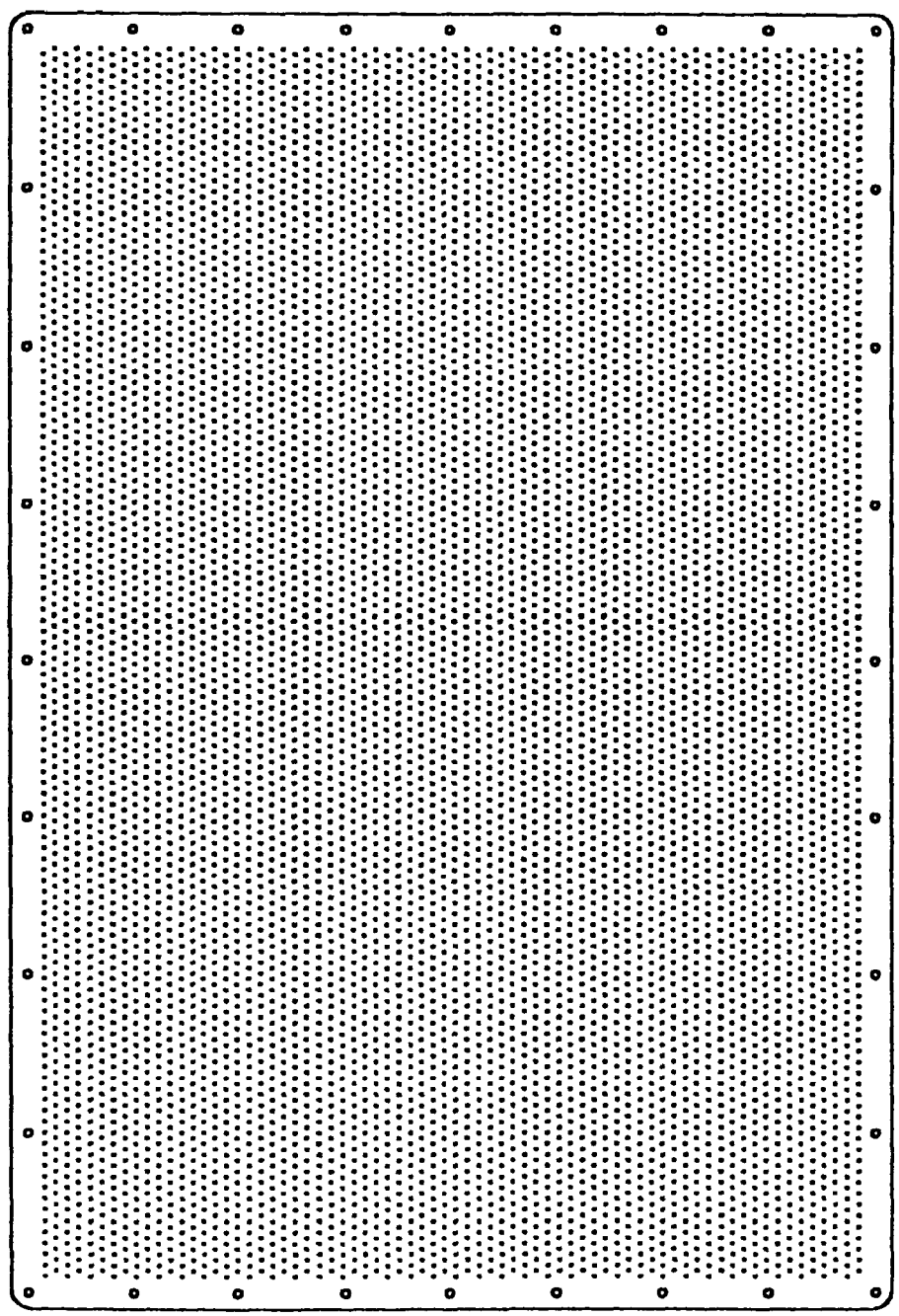
FIG. 17a is a top planar view of a scar-reduction resorbable healing membrane in accordance with a fifteenth pre-formed embodiment of the present invention.

FIG. 2a illustrates a laminotomy procedure wherein a the two vertebrae 20 and 22 are separated and fixated using screws 24 and rods 26, and a portion of the lamina has been removed, leaving a window 28 (shown as a phantom rectangle) in the vertebrae 22. FIG. 2b is an enlarged view of the window 28 in the lamina of the vertebrae 22. The spinal chord 30 and an exiting nerve root 32 are thus exposed. In accordance with the present invention, the scar-reduction resorbable healing membrane is applied to the dura of both the spinal chord 30 and the exiting nerve root 32, to thereby attenuate or eliminate the occurrence of post-operative scarring in the vicinity of the exiting nerve root 32. In a modified embodiment, a thicker bridging healing membrane is applied to one or both of the vertebrae 20 and 22, to thereby bridge (i.e., tent) over and cover the window 28. This bridging healing membrane may be non-porous, fluid permeable, cell permeable or vessel permeable in accordance with various embodiments, and preferably comprises a thickness between about 0.5 mm and 2.0 mm for preventing prolapse of adjacent muscle tissue into the foramen (i.e., the spinal lumen containing the spinal chord 30 and exiting nerve root 32). In accordance with various embodiments, the bridging healing membrane may be used alone or in combination with the scar-reduction resorbable healing membrane or, the scar-reduction resorbable healing membrane may be used without the bridging healing membrane.

In accordance with one aspect of the present invention, the scar-reduction resorbable healing membrane can be heat bonded, such as with a bipolar electro-cautery device, ultrasonically welded, or similarly sealed directly to the dura of the spinal chord 30 and the exiting nerve root 32. Such a device can be used to heat the healing membrane at various locations, such as at the edges and at points in the middle, at least above its glass transition temperature, and preferably above its softening point temperature. The glass transition temperature of the preferred material is about 55° Celsius, while its softening point temperature is above 110° Celsius. The material is heated along with adjacent tissue such that the two components bond together at their interface. In another embodiment, the scar-reduction resorbable healing membrane can be heat bonded or sealed directly to one or both of the vertebrae 20 and 22, or to muscle or other soft tissue, for example. In yet another embodiment, the scar-reduction resorbable healing membrane can be heat bonded or sealed directly to itself in an application, for example, wherein the healing membrane is wrapped around a structure and then heat joined to itself. Moreover, the technique of heat-sealing the healing membrane material to itself or body tissue may be combined with another attachment method for enhanced anchoring. For example, the healing membrane material may be temporarily affixed in position using two or more points of heat sealing (i.e., heat welding) using an electro-cautery device, and sutures, staples or glue can then be added to secure the healing membrane into place.

Figure 18:
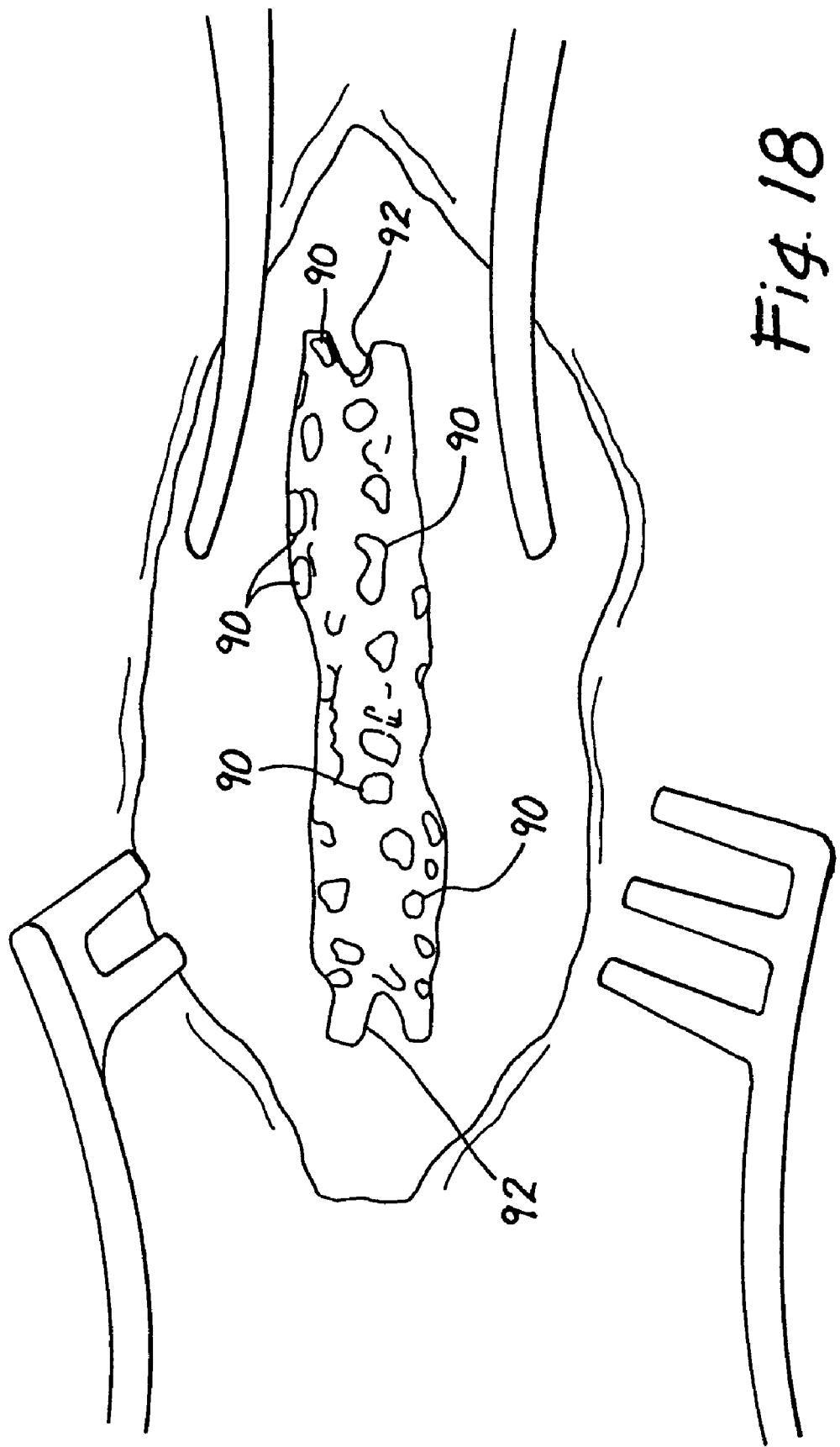
FIG. 18 is illustrates a scar-reduction resorbable healing membrane implanted on a rat spine, with two spinus processes of the spine protruding at opposing ends of the implant.

Turning to FIG. 3, a pre-formed scar-reduction resorbable healing membrane 34 is formed with a first welding flange 36 and a second welding flange 38 thereon. A trunk portion 40 fits over the spinal chord 30, and a branch portion 42 fits over the exiting nerve root 32. The first welding flange 36 is formed by a first slit 44 and a second slit 46, and the second welding flange 38 is formed by a first slit 48 and a second slit 50. In application, the pre-formed scar-reduction resorbable healing membrane 34 is placed over the spinal chord 30 and the exiting nerve root 32 and, subsequently, the first welding flange 36 and the second welding flange 38 are bent at least partially around the exiting nerve root. The rounded end 52 of the branch portion 42 fits onto a portion of the exiting nerve root 32 furthest away from the spinal chord 30. As presently embodied, the first welding flange 36 and the second welding flange are wrapped around, and preferably tucked beneath (i.e., behind) the exiting nerve root 32. In a preferred embodiment, the first welding flange 36 is then heat welded to the second welding flange 38. The flanges preferably are cut to wrap entirely around the exiting nerve root 32 and overlap one another. The first welding flange 36 may be sutured to the second welding flange 38, alone or in addition with the heat welding step, to thereby secure the first welding flange 36 to the second welding flange 38. In another embodiment, neither heat welding nor suturing is used and the flanges are merely tucked partially or completely around the exiting nerve root 32 (depending on the dimensions of the root 32). When sutures are to be used, the pre-formed scar-reduction resorbable healing membrane 34 may be pre-formed and packaged with optional suture apertures 60. The edges 64 and 66 are then preferably heat welded to the spinal chord 30. The two edges 68 and 70 form a third welding flange 72. A fourth welding flange 74 is formed by slits 76 and 78, and a fifth welding flange 80 is formed by slits 82 and 84. The welding flanges may be secured in manners similar to those discussed in connection with the welding flanges 36 and 38. Heat welds may further be secured along other edges and along the surface of the pre-formed scar-reduction resorbable healing membrane 34, such as shown at 90 in FIG. 18. Moreover, notches may be formed on the healing membranes of the present invention, such as, for example, at the ends 64 and 66 in modified-shape embodiments, for accommodating, for example, the spinal processes. Such exemplary notches are shown in FIG. 18 at 92.

FIG. 4 illustrates a scar-reduction resorbable healing membrane for application to two exiting nerve roots 32 and 98 of the spinal chord in accordance with another pre-formed embodiment of the present invention. FIG. 5 illustrates a scar-reduction resorbable healing membrane similar to that of FIG. 4 but adapted for application to four exiting nerve roots of the spinal chord in accordance with another pre-formed embodiment of the healing membrane. For example, the branch portion 100 is analogous in structure and operation to the branch portion 42 of the FIG. 3 embodiment, and the other branch portion 102 is constructed to accommodate the exiting nerve root 98. Similar elements are shown in FIG. 5 at 100*a*, 102*a*, 100*b* and 102*c*. The embodiments of FIGS. 6-17 illustrate other configurations for accommodating different anatomical structures. For example, the configurations of FIGS. 7, 10, 12, 14 and 15 are designed to be formed into, for example, a cone structure to fit around a base portion with a protrusion extending through the center of the healing membrane. The illustrated embodiments of FIGS. 6-17 have suture perforations formed around their perimeters, and many are shown with cell and vessel permeable pores. The various embodiments illustrated in FIGS. 3-17*b* may be used for example to facilitate the healing of cardiac and/or pericardiac tissues in accordance with the methods disclosed herein.

In accordance with the present invention, the pre-formed scar-reduction resorbable healing membranes are preformed and sealed in sterilized packages for subsequent use by the surgeon. Since an objective of the scar-reduction resorbable healing membranes of the present invention is to reduce sharp edges and surfaces, preformation of the healing membranes is believed to help facilitate, albeit to a relatively small degree, rounding of the edges for less rubbing, tissue turbulence and inflammation. That is, the surfaces and any sharp edges of the scar-reduction resorbable healing membranes are believed to be capable of slightly degrading over time in response to exposure of the healing membranes to moisture in the air, to thereby form rounder edges. This is believed to be an extremely minor effect. Moreover, sterilization processes (E-beam or heat) on the cut, pre-packaged and/or packaged healing membrane can further round any sharp edges, as can any initial heating to glass temperature of the pre-cut healing membranes just before implanting. Moreover, the very thin scar-reduction resorbable healing membranes of the present invention may be particularly susceptible to these phenomena, and, perhaps to a more noticeable extent, are susceptible to tearing or damage from handling, thus rendering the pre-forming of the scar-reduction resorbable healing membranes beneficial for preserving the integrity thereof.

An embodiment of the scar-reduction resorbable healing membrane has been tested in rat studies in comparison with several scar-tissue reduction barrier gels with favorable results. Specifically, the healing membrane material of the present invention and the scar-tissue reduction gels were inserted around the spinal column of 52 male adult Sprague-Dawley rats, each weighing 400 plus grams. A posterior midline incision was made exposing the bony posterior elements from L4 to L7, and bilateral laminectomies were performed at the L5 and L6 level using surgical loupes. Following the laminectomies, the dura was retracted medially (to the left then to the right) using a microscope to expose the disc at L5/L6, and a bilateral controlled disc injury was performed using a 26 gauge needle. After hemostasis and irrigation, an anti-inflammatory agent was applied over both laminectomy sites.

The rats were divided and treated in five groups: 1) normal controls without surgery; 2) untreated, laminectomy only; 3) those to which 0.1 cc of high molecular weight hyaleronan (HA gel) was applied to the laminectomy site; 4) those to which 0.1 cc of Adcon-L scar-tissue reduction gel was applied to the laminectomy site; and 5) those that had an insertion of a healing membrane of the present invention over the laminectomy site. The wounds were closed in a routine manner, and the survival period was three weeks.

After termination of each of the rats, the L5 segmental nerve roots were dissected free bilaterally using an anterior approach. The segmental nerve roots were excised including the portion of the nerve root within the foramen (1 cm in length). Additionally, the dura was exposed using an anterior approach. The dura from the caudal aspect of the body of L4 to the cephalad aspect of the body of L7 was removed (1.5 center in length) including all attached scar. The samples were analyzed biochemical by extracting the fat, then vacuum drying and determining the amount of total collagen and the percent of collagen from the hydroxyproline content. The amount of total collagen was expressed in milligrams and the percent of collagen was expressed as a percent of fat free dry weight.

Each treatment group was compared to both the normal controls and the operated but untreated controls using a Fisher's multiple comparisons paired t-test. Additionally, the treatment groups were compared using a one-way analysis of variance. In the untreated, laminotomy-only specimens, the total collagen increased more than two-fold in the dura (p value of 0.0009). In the untreated group, the percent collagen increased significantly in both the dura and nerve roots (p values of 0.001 and 0.005, respectively). Treatment with HA gel (p=0.010), Adcon-L (p=0.004), or the healing membrane of the present invention (p=0.002) significantly reduced the amount of total collagen in the dura. Likewise, the same holds true for the percent collagen where the values are: HA gel (p=0.015), Adcon-L (p=0.041), and the healing membrane of the present invention (p=0.011). There was a trend showing that the healing membrane of the present invention decreased approximately 50% more both in total collagen and percent collagen compared to the HA gel and Adcon-L. In the nerve roots, the amount of total collagen and a percentage of collagen was not significantly changed by treatment with any of the HA gel, Adcon-L, or healing membrane of the present invention.

These biochemical measurements of total and percent collagen enabled obtension of quantitative data on scar formation post laminotomy. Gross findings and biochemical analysis in the model demonstrated that the untreated laminotomy scar becomes adherent to the dorsum of the dura mater, a clearly undesirable outcome. Both a single application of HA gel or Adcon-L demonstrated a beneficial effect at the level of the dura. However, the half life of HA gel is less than 24 hours, and the Adcon-L is resorbed within approximately four weeks, which suggests that further long-term studies could be conducted. Additionally, Adcon-L has the potential to delay posterior wound healing, possibly leading to wound infections and/or wound dehiscences (few of the adverse events experienced by less than 1% of the study groups per product pamphlet). On the other hand, the healing membrane of the present invention appears to wall off the overlying muscle, potentially protecting against cellular trafficking and vascular ingrowth, and does not appear to interfere with normal posterior wound healing. A possible improvement on the results obtained by using the healing membrane of the present invention by itself may be obtained by using the healing membrane in conjunction with an anti-inflammatory gel agent applied, for example, beneath the healing membrane. Additionally, the scar-tissue reduction healing membrane may be used in combination with a fixation device for stabilizing the bone defect, such as shown in connection with the two vertebrae 20 and 22 of FIG. 1.

Figure 19:
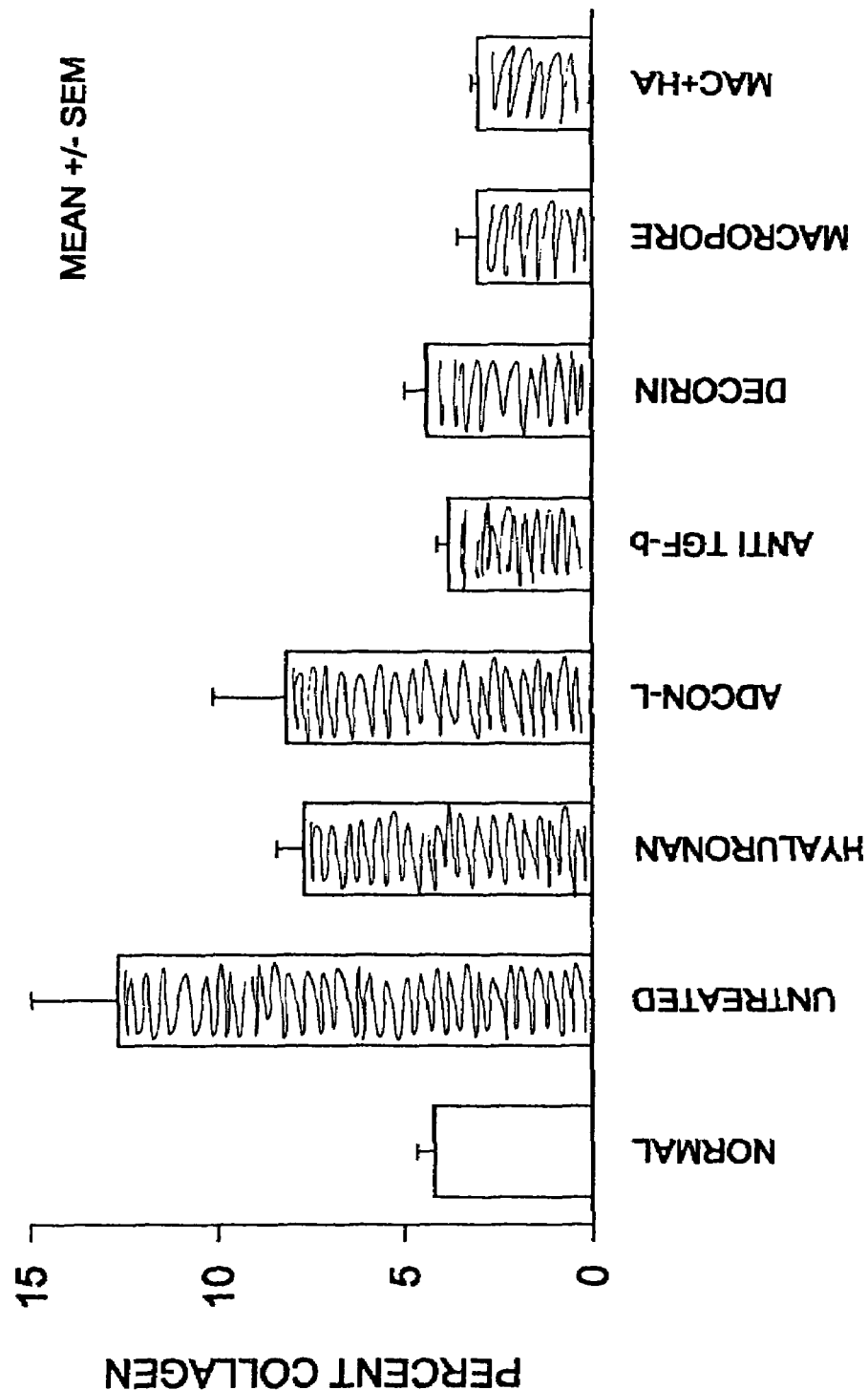
FIG. 19 is a bar graph showing the results of a study comparing the scar-reduction healing membrane of the present invention against several other materials, and controls, indicating the percent collagen found in and around the dura following a surgical procedure after a period of about three weeks.

FIG. 19 illustrates a bar graph showing the percent collagen resulting from the aforementioned rat tests for various groups. The results for the healing membrane of the present invention are labeled as Macropore, while the last result denoted MAC+HA is for the healing membrane material of the present mention in conjunction with HA gel. The results indicate that there is a marked improvement over the HA gel or Adcon-L, and significant improvement in comparison with a tissue growth factor beta and a material known as Decorin.

In one embodiment, the healing membrane may be used in a number of other surgical applications, including: surgical repair of fracture orbital floors, surgical repair of the nasal septum and perforated ear drum healing membrane, as a protective sheathing to facilitate osteogenesis, surgical repair of the urethral anatomy and repair of urethral strictures, prevention of synostosis in completed corrective surgery for cranial fusions and forearm fractures, lessening of soft-tissue fibrosis or bony growth, as a temporary covering for prenatal rupture omphalocele during staged repair procedures, guided tissue regeneration between the teeth and gingival margin, tympanic healing membrane repairs, dural coverings and neural repair, heart vessel repair, hernia repair, tendon anastomoses, temporary joint spacers, wound dressings, scar coverings, and as a covering for gastroschisis.

Applicants hereby incorporate the entire disclosures of U.S. Pat. No. 6,531,146, and all patents and other references cited therein, by reference.

While the foregoing is a complete description of the preferred embodiments of the invention, various alternatives, modifications, and equivalents may be used. Furthermore, although the disclosure herein refers to certain illustrated embodiments, it is to be understood that these embodiments are presented by way of example and not by way of limitation. The intent of the following detailed description is to cover all modifications, alternatives, and equivalents as may fall within the spirit and scope of the invention.

What is claimed is:

1. A method for promoting healing of damaged tissue after an open heart surgery, the method comprising:
   providing a substantially planar healing membrane, which is: (a) substantially-smooth on at least one side; (b) substantially uniform in composition; (c) about 10 microns to about 300 microns in thickness; (d) non-porous; (e) constructed from a resorbable polymer base material being a poly-lactide polymer and a copolymer of lactides, the poly-lactide polymer and copolymer of lactides being 70:30 poly (L-lactide-co-D,L-lactide); and (f) adapted to be resorbed into the mammalian body within a period of approximately 18 to 24 months from an initial implantation of the membrane into the mammalian body; and
   placing the healing membrane adjacent to an opening in pericardial tissue of a patient so that the pericardial tissue surrounding the opening can regenerate over the membrane.

2. A method for promoting healing of damaged tissue after an open heart surgery, the method comprising:
   providing a substantially planar healing membrane, which is: (a) substantially-smooth on at least one side; (b) substantially uniform in composition; (c) about 10 microns to about 300 microns in thickness; (d) non-porous; (e) constructed from a resorbable polymer base material being a poly-lactide polymer and the poly-lactide polymer being poly-L-lactide; and (f) adapted to be resorbed into the mammalian body within a period of approximately 18 to 24 months from an initial implantation of the membrane into the mammalian body; and placing the healing membrane adjacent to an opening in pericardial tissue of a patient so that the pericardial tissue surrounding the opening can regenerate over the membrane.

3. The method of claim 1 wherein the thickness of the membrane is about 100 microns.

4. The method of claim 1 wherein the thickness of the membrane is about 200 microns.

5. The method of claim 1 wherein the healing membrane is provided in a sterile packaging.

6. A method for promoting healing of damaged tissue after an open heart surgery, the method comprising:

providing a substantially planar healing membrane, which is: (a) substantially-smooth on at least one side; (b) substantially uniform in composition; (c) about 10 microns to about 300 microns in thickness; (d) non-porous; (e) constructed from a resorbable polymer base material selected from the group consisting essentially of (i) a poly-lactide polymer, (ii) a copolymer of lactides, and (iii) a poly-lactide polymer and a copolymer of lactides; and (f) adapted to be resorbed into the mammalian body within a period of approximately 18 to 24 months from an initial implantation of the membrane into the mammalian body; and placing the healing membrane adjacent to an opening in pericardial tissue of a patient so that the pericardial tissue surrounding the opening can regenerate over the membrane, the placing of the healing membrane in a patient being effective to attenuate formation of scar tissue.

7. The method of claim 1 wherein the step of placing the healing membrane in a patient is effective to attenuate tissue adhesion.

8. The method of claim 1 further comprising a step of attaching the healing membrane to the pericardial tissue.

9. The method of claim 8 wherein the attaching step comprises heat bonding the membrane to the pericardial tissue.

10. A method for promoting healing of damaged tissue after an open heart surgery, the method comprising:

providing a substantially planar healing membrane, which is: (a) substantially-smooth on at least one side; (b) substantially uniform in composition; (c) about 10 microns to about 300 microns in thickness; (d) non-porous; (e) constructed from a resorbable polymer base material selected from the group consisting essentially of (i) a poly-lactide polymer, (ii) a copolymer of lactides, and (iii) a poly-lactide polymer and a copolymer of lactides, the membrane comprising angiotensin antagonists; and (f) adapted to be resorbed into the mammalian body within a period of approximately 18 to 24 months from an initial implantation of the membrane into the mammalian body; and placing the healing membrane adjacent to an opening in pericardial tissue of a patient so that the pericardial tissue surrounding the opening can regenerate over the membrane.

11. The method of claim 1, wherein the healing membrane is precontoured into a heart-shaped bag and the placing comprises placing the healing membrane to surround the apex of a heart.

12. A method for promoting healing of damaged tissue after an open heart surgery, the method comprising:

providing a substantially planar healing membrane, which is: (a) substantially-smooth on at least one side; (b) substantially uniform in composition; (c) about 10 microns to about 300 microns in thickness; (d) non-porous; (e) constructed from a resorbable polymer base material selected from the group consisting essentially of (i) a poly-lactide polymer, (ii) a copolymer of lactides, and (iii) a poly-lactide polymer and a copolymer of lactides, the healing membrane being precontoured into a tube; and (f) adapted to be resorbed into the mammalian body within a period of approximately 18 to 24 months from an initial implantation of the membrane into the mammalian body; and placing the healing membrane adjacent to an opening in pericardial tissue of a patient so that the pericardial tissue surrounding the opening can regenerate over the membrane, the placing comprising placing the healing membrane around the conduit of a left-ventricular assist device (LVAD).

13. A method for promoting healing of damaged tissue after an open heart surgery, the method comprising:

providing a substantially planar healing membrane, which is: (a) substantially-smooth on at least one side; (b) substantially uniform in composition; (c) about 10 microns to about 300 microns in thickness; (d) non-porous; (e) constructed from a resorbable polymer base material selected from the group consisting essentially of (i) a poly-lactide polymer, (ii) a copolymer of lactides, and (iii) a poly-lactide polymer and a copolymer of lactides, the healing membrane being precontoured; and (f) adapted to be resorbed into the mammalian body within a period of approximately 18 to 24 months from an initial implantation of the membrane into the mammalian body; and placing the healing membrane adjacent to an opening in pericardial tissue of a patient so that the pericardial tissue surrounding the opening can regenerate over the membrane, the placing comprising placing the healing membrane over a pump of a left-ventricular assist device (LVAD).

* * * * *